(12) United States Patent
Sezi et al.

(10) Patent No.: US 6,310,238 B1
(45) Date of Patent: *Oct. 30, 2001

(54) O-AMINO(THIO)PHENOLCARBOXYLIC ACIDS, AND THEIR PREPARATION

(75) Inventors: Recai Sezi, Röttenbach; Michael Keitmann, Weisendorf, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/161,147

(22) Filed: Sep. 24, 1998

(30) Foreign Application Priority Data

Sep. 24, 1997 (DE) ................................................ 197 42 194

(51) Int. Cl.⁷ ........................ C07C 229/10; C07C 229/12
(52) U.S. Cl. ............................ 562/433; 562/441; 562/457
(58) Field of Search .................................... 562/457, 441, 562/433

(56) References Cited

FOREIGN PATENT DOCUMENTS

| | | |
|---|---|---|
| 0023662 | 5/1983 | (EP) . |
| 0264678 | 9/1991 | (EP) . |
| 811758 | 4/1959 | (GB) . |
| 1283476 | 7/1972 | (GB) . |

*Primary Examiner*—Alan L. Rotman
*Assistant Examiner*—Rita Desai

(57) ABSTRACT

The invention relates to novel o-aminophenolcarboxylic acids or o-aminothiophenolcarboxylic acids of the following structure

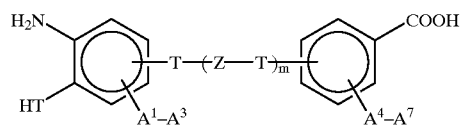

in which:

$A^1$ to $A^7$ are—independently of one another—H, $CH_3$, $OCH_3$, $CH_2CH_3$ or $OCH_2CH_3$;

T is O or S, and m is 0 or 1;

Z is a carbocyclic or heterocyclic aromatic radical.

11 Claims, No Drawings

O-AMINO(THIO)PHENOLCARBOXYLIC ACIDS, AND THEIR PREPARATION

BACKGROUND OF THE INVENTION

1. Field of the Invention

The invention relates to novel o-aminophenolcarboxylic acids and o-aminothiophenolcarboxylic acids, which are also jointly abbreviated to o-amino(thio)phenolcarboxylic acids, and to a process for their preparation.

o-Aminophenolcarboxylic acids are needed, in particular, for the preparation of high-temperature-stable polymers, such as polybenzoxazoles (PBOs) and their precursors. Compared with the preparation of polybenzoxazoles or PBO precursors from bis-o-aminophenols and dicarboxylic acids, the use of o-aminophenolcarboxylic acids has significant advantages. For example, an o-aminophenolcarboxylic acid can be reacted with itself, i.e. a second monomer is not absolutely necessary for the polymerization. This allows purity monitoring and storage to be simplified. In addition, the stoichiometry is predefined, i.e. errors in the calculation or weighing-out of the reactants, as can occur in the reaction of bis-o-aminophenols with dicarboxylic acids, are excluded if o-aminophenolcarboxylic acids are used. Furthermore, the nature of the monomer used has a strong effect on the property profile of the PBO precursor or polybenzoxazole prepared therewith. For example, not only the thermal, electrical and mechanical behavior, but also the solubility and hydrolysis stability and numerous other properties of the polymer are greatly affected by the monomer used in the preparation.

PBO precursors in the form of a photosensitive composition can be structured inexpensively by direct methods, i.e. without an auxiliary resist. Compared with other dielectrics which can be photostructured directly, such as polyimide (PI) and benzocyclobutene (BCB), PBO precursors offer the advantage of positive structurability and aqueous-alkaline development (see EP 0 023 662 B1 and EP 0 264 678 B1). To this end, the PBO precursors used must be substantially transparent at the exposure wavelength and sufficiently soluble in the developer, which preferably contains no metal ions. Like polyimides, polybenzoxazoles also have the major advantage that they—compared with the cyclized final product—as readily soluble precursors, can be applied to a substrate and then cyclized, during which the solubility and thus the sensitivity to solvents and other process chemicals decreases greatly.

Besides good solubility of the precursors, advantages for the use of polybenzoxazoles in microelectronics are low moisture absorption and a good planarization capacity. Production of components using a dielectric which produces good planarization allows expensive polishing procedures (chemical mechanical polishing, CMP) to be avoided.

o-Aminophenolcarboxylic acids are disclosed, for example, in GB 811,758 and GB 1,283,476. In PBO films produced from the known monomers, the water absorption in boiling water after 24 h is 0.77%. No mention is made of the planarization behavior of the polymers produced after cyclization on the substrate or their suitability as base polymers for compositions which can be photostructured positively.

SUMMARY OF THE INVENTION

The object of the invention is to provide o-aminophenolcarboxylic acids and o-aminothiophenolcarboxylic acids which are suitable for the preparation of polymers which satisfy the greatly increased demands of microelectronics. The o-amino(thio)phenolcarboxylic acids should, in particular, enable the preparation of readily soluble polymer precursors which, after cyclization on a substrate, give polybenzoxazoles or polybenzothiazoles of low moisture absorption and high degree of planarization.

This is achieved in accordance with the invention by o-aminophenolcarboxylic acids and o-aminothiophenolcarboxylic acids of the following structure:

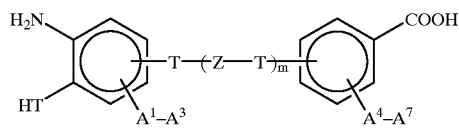

in which $A^1$ to $A^7$ are—independently of one another—H, $CH_3$, $OCH_3$, $CH_2CH_3$ or $OCH_2CH_3$;

T is O or S,; m is 0 or 1;

Z is one of the following carbocyclic or heterocyclic aromatic radicals:

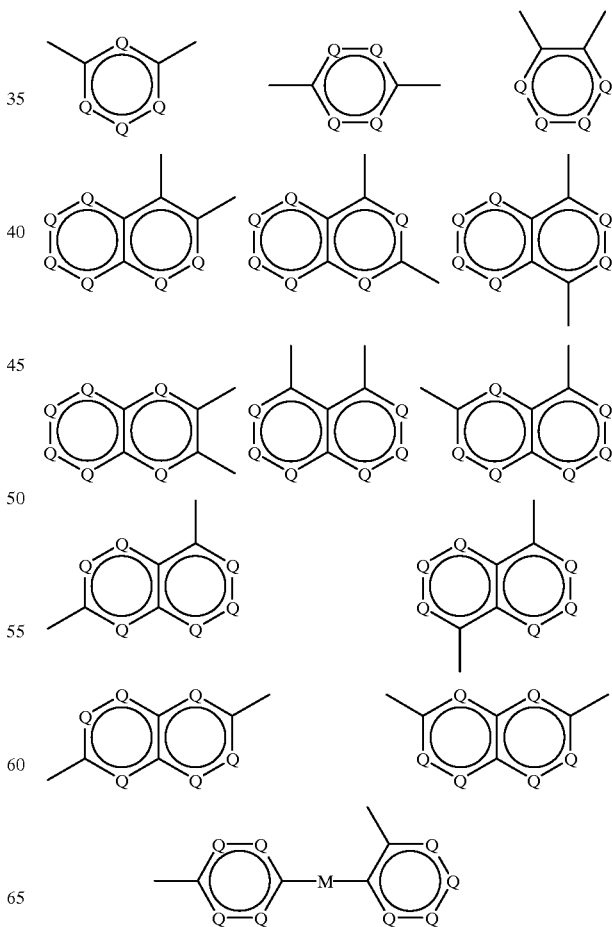

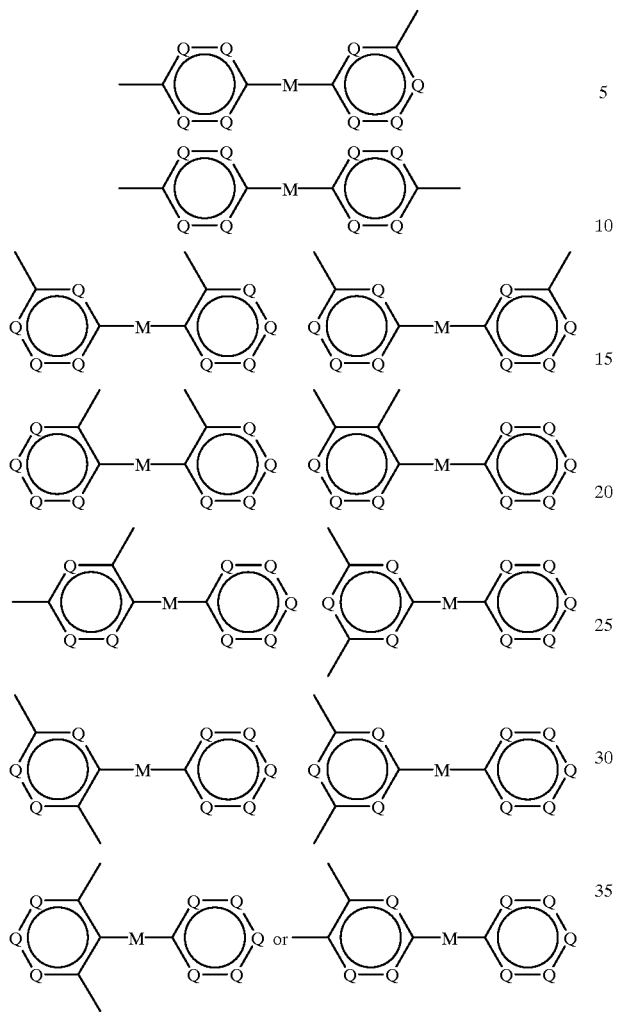

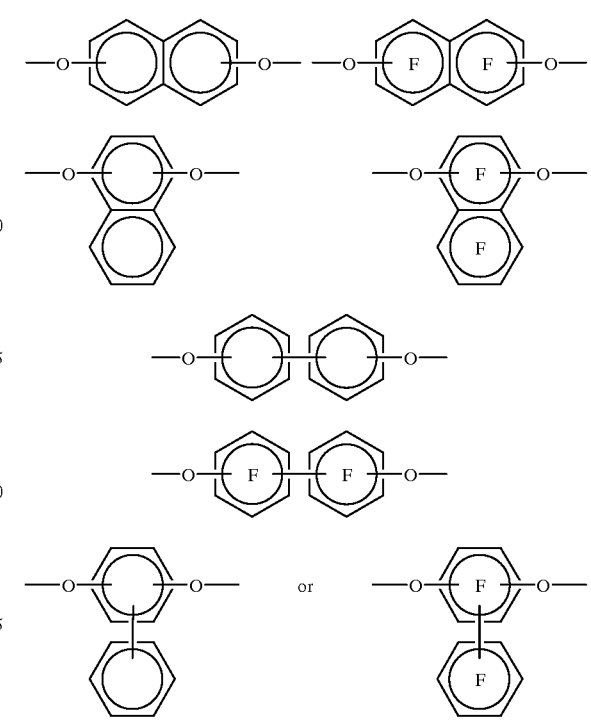

wherein Q=C—A or N, and A=H, F, $(CH_2)_pCH_3$, $(CF_2)_pCF_3$, $O(CH_2)_pCH_3$, $O(CF_2)_pCF_3$, $CO(CH_2)_pCH_3$, $CO(CF_2)_pCF_3$ where p=0 to 8 (linear or branched chain), $OC(CH_3)_{31}$, $OC(CF_3)_3$, $C_6H_5$, $C_6F_5$, $OC_6H_5$, $OC_6F_5$, cyclopentyl, perfluorocyclopentyl, cyclohexyl or perfluorocyclohexyl, where, in the isolated aromatic rings, a maximum of 3 nitrogen atoms may be present per ring and only 2 nitrogen atoms may be adjacent, and, in the fused ring systems, a maximum of 2 nitrogen atoms may be present per ring, M=a single bond, $(CH_2)_n$, $(CF_2)_n$, $CH(CH_3)$, $CH(CF_3)$, $CF(CH_3)$, $CF(CF_3)$, $C(CH_3)_2$, $C(CF_3)_2$, $CH(C_6H_5)$, $CH(C_6F_5)$, $CF(C_6H_5)$, $CF(C_6F_5)$, $C(CH_3)(C_6H_5)$, $C(CH_3)(C_6F_5)$, $C(CF_3)(C_6H_5)$, $C(CF_3)(C_6F_5)$, $C(C_6H_5)_2$, $C(C_6F_5)_2$, CO, $SO_2$

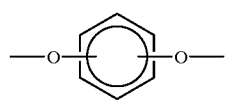 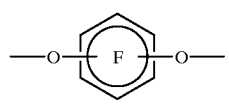

with the proviso that, when m=0, a 3-amino-4-hydroxyphenoxy group cannot be in the p-position to the carboxyl group.

The novel compounds have, for example, the following preferred structure:

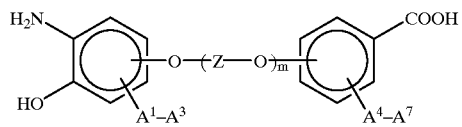

In compounds of this type, the ether bridges are apparently responsible for the good solubility and the good planarization properties of the polymer precursors prepared therewith. By the way, the characterization "$A^1$–$A^3$" and "$A^4$–$A^7$" in the structural formula means that the aminophenyl groups and carboxyphenyl groups contain radicals $A^1$, $A^2$ and $A^3$, and $A^4$, $A^5$, $A^6$ and $A^7$ respectively.

The o-amino(thio)phenolcarboxylic acids can be prepared by (a) reacting a halogen compound of the structure

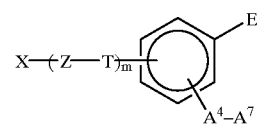

with a nitrophenol or nitrothiophenol (abbreviated to "nitro(thio)phenol") of the structure

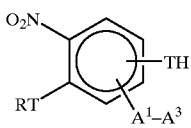

in the presence of at least a stoichiometric amount of a base, or with an alkali metal salt of the nitro(thio) phenol, in a solvent at a temperature between −10 and 80° C., where X is a halogen atom, E is CN or $COOR^1$, where $R^1$=alkyl (having 1 to 5 carbon atoms), phenyl or benzyl, $A^1$ to $A^7$, T and Z are as defined above, and R is one of the following radicals: alkyl, alkoxyalkyl, alkenyl, alkoxyalkenyl, alkynyl or alkoxyalkynyl, each having a maximum of 6 carbon atoms, phenyl, phenacyl or benzyl, and benzylalkyl, benzylalkenyl, benzyloxyalkyl, benzyloxyalkenyl, benzylalkoxyalkyl or benzylalkoxyalkenyl, each having a maximum of 4 aliphatic carbon atoms; and (b) reducing and hydrolyzing the resultant nitro compound to the amino compound, and removing the group R.

In this synthesis, which is very economical, a halogen-containing ester or a corresponding nitrile is thus reacted with a nitro(thio)phenol having an R-protected hydroxyl or mercapto group in the opposition to the nitro group. The nitro compound formed is then reduced to the corresponding amino compound, the ester or nitrile group is hydrolyzed to the carboxyl group, and the protecting group R is removed Alternatively, the o-amino(thio)phenolcarboxylic acids can also be prepared by (a) reacting a nitro compound of the structure

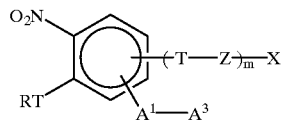

with a phenol or thiophenol (abbreviated to (thio) phenol) of the structure

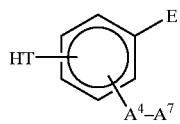

in the presence of at least a stoichiometric amount of a base, or with an alkali metal salt of the (thio)phenol, in a solvent at a temperature between −10 and 80° C., where X is a halogen atom, E is CN or $COOR^1$, where $R^1$=alkyl (having 1 to 5 carbon atoms), phenyl or benzyl, $A^1$ to $A^7$, T and Z are as defined above, and R is one of the above mentioned radicals; and (b) reducing and hydrolyzing the resultant nitro compound to the amino compound, and removing the group R.

In this preparation process, which is likewise very economical, a halogen-containing nitro compound having a protected hydroxyl or mercapto group in the opposition to the nitro group is thus reacted with a (thio)phenol containing an ester or nitrile group. The nitro compound formed is then—in the manner indicated above—subjected to a reduction, hydrolysis and removal of protecting group.

The preparation of nitro(thio)phenols containing a protected hydroxyl or mercapto group in the opposition to the nitro group has been described in the parallel German patent application serial no. 197 42 135.0 "o-Nitro(thio)phenol derivatives, and their preparation" (docket GR 97 P 3683).

DESCRIPTION OF PREFERRED EMBODIMENTS

The protecting group R is preferably an alkyl, alkoxyalkyl, phenyl or benzyl group. It is an important advantage that the radical RT is stable in the reaction between the halogen compound and the nitro(thio)phenol, but can subsequently be removed.

The reaction between the halogen compound and the nitro(thio)phenol, in which an ether or thioether bridge is formed, is carried out in the presence of a base. This base is preferably a carbonate or hydrogencarbonate of an alkali metal or alkaline earth metal, such as sodium carbonate or potassium carbonate. Formation of the (thio)ether requires at least a stoichiometric amount of the base. It may also be advantageous to use an organic base containing a tertiary N atom, for example triethylamine or pyridine.

The nitro(thio)phenol can also be replaced by a corresponding alkali metal salt, for example the potassium salt. In this case, a base is not absolutely necessary for the reaction with the halogen compound.

A reaction temperature in the range from −10 to 80° C. has proven suitable. Temperatures ≦80° C. are preferred owing to the greater selectivity of the reaction.

Suitable solvents are, in particular, dimethylformamide, diethylformamide, dimethylacetamide, dimethyl sulfoxide, N-methylpyrrolidone, γ-butyrolactone, acetonitrile, tetrahydrofuran and pyridine. In principle, however, all polar aprotic solvents in which the starting compounds are soluble can be used.

The reduction of the nitro compound can be carried out, for example, by catalytic hydrogenation using, for example hydrogen on Pd/C catalyst. In principle, however, all the processes which are suitable for reducing the nitro group to the amino group are suitable. The hydrolysis of the ester or nitrile group can be carried out, for example, using potassium hydroxide. The protecting group can be removed using, for example, trifluoroacetic acid or titanium tetrachloride. These reactions can be carried out in separate process steps; the sequence of the process steps is unimportant.

It is also possible to remove the protecting group and carry out the hydrolysis simultaneously, i.e. in one step. In the presence of an ester group, these two reactions are particularly advantageously carried out together with the reduction of the nitro group, preferably by hydrogenation using hydrogen on Pd/C. Hydrogenation is preferably carried out at temperatures of from 25 to 50° C. Suitable solvents are esters and ethers, for example ethyl acetate and tetrahydrofuran.

The polymer precursors prepared from the o-amino(thio) phenolcarboxylic acids of the invention and having improved properties compared with the prior art are soluble in many organic solvents, such as acetone, cyclohexanone, N-methylpyrrolidone, diethylene glycol mono- or diethyl ether, ethyl lactate and γ-butyrolactone, and in aqueous-alkaline developers containing no metal ions. They are therefore highly suitable as base polymers for dielectrics which can be photostructured positively and can be developed in aqueous-alkaline media. The precursors can easily be applied to substrates, such as silicone wafers, by spin-coating methods, they form uniform films, and can readily be cyclized on the substrate. A particular advantage of the precursors prepared from these o-amino(thio) phenolcarboxylic acids is their high planarization capacity and low moisture absorption.

The invention will be illustrated in greater detail below with reference to working examples.

EXAMPLE 1

Preparation of 4-(4-benzyloxycarbonylphenoxy) nonafluorobiphenyl

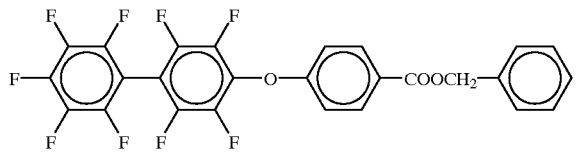

37.4 g of decafluorobiphenyl (0.112 mol) are dissolved in 700 ml of dimethylformamide, the mixture is cooled to −10° C. using a cryostat, and a solution of 29.8 g of potassium 4-benzyloxycarbonylphenoxide (0.112mol) in 300 ml of dimethylformamide is then added dropwise over the course of 2 hours. After 48 hours at −10° C., the potassium salt has reacted. The dimethylformamide is then removed in a rotary evaporator, the residue is taken up in a little tetrahydrofuran, and the solution is filtered through a silica-gel column. The clear solution obtained is evaporated in a rotary evaporator until a white solid precipitates out. The solid is then stirred in n-hexane, filtered off using a fluted filter and then dried for 48 hours under nitrogen at 40° C./10 mbar in a vacuum drying cabinet (yield: 92%).

Characterization:

| Mass spectrum: molecular peak at 542 Elemental analysis | |
| --- | --- |
| Theoretical value (in %) | C: 57.6 H: 2.0 |
| Found (in %) | C: 57.5 H: 1.9 | m.p.: 120° C.

EXAMPLE 2

Preparation of 4-(4-nitro-3-benzyloxyphenoxy)-4'-(4-benzyloxycarbonylphenoxy)octafluorobiphenyl

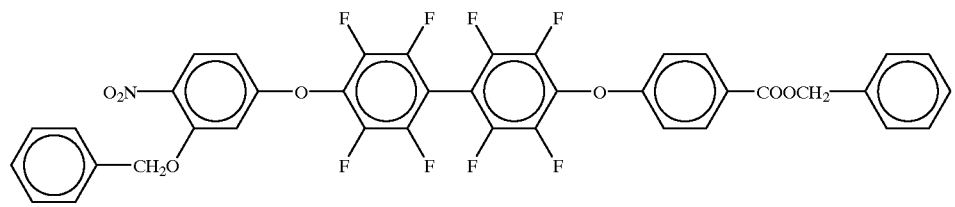

49.9 g of the 4-(4-benzyloxycarbonylphenoxy) nonafluorobiphenyl (0.092 mol) prepared as described in Example 1 and 26.1 g of potassium 4-nitro-3-benzyloxyphenoxide (0.092 mol) are dissolved in 400 ml of dimethylformamide, and the solution is heated to 80° C.; the reaction is complete after 24 hours. The solvent is then removed in a rotary evaporator. The solid residue obtained is washed three times with methanol, filtered off via a Büchner funnel and subsequently dried for 48 hours under nitrogen, at 40° C./10 mbar in a vacuum drying cabinet (yield: 94%).

Characterization:

| Mass spectrum: molecular peak at 767 Elemental analysis | |
| --- | --- |
| Theoretical value (in %) | C: 61.0 H: 2.8 N: 1.8 |
| Found (in %) | C: 60.8 H: 2.7 N: 1.9 | m.p.: 152° C.

EXAMPLE 3

Preparation of 4-(4-amino-3-hydroxyphenoxy)4'-(4-carboxyphenoxy)octafluorobiphenyl

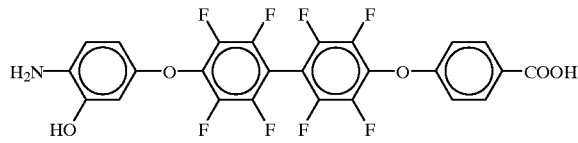

49.9 g of the 4-(4-nitro-3-benzyloxyphenoxy)-4'-(4-benzyloxycarbonylphenoxy)octafluorobiphenyl (0.065 mol) prepared as described in Example 2 are dissolved in 400 ml of a mixture of tetrahydrofuran and ethyl acetate (volume ratio 1:1), and 5 g of Pd/C (palladium/carbon) are then added to the solution. The mixture is then hydrogenated using hydrogen at a pressure of 1 bar at room temperature in an autoclave with vigorous stirring; the reaction is terminated after 3 days. The yellow-beige solution is evaporated to half in a rotary evaporator and left to stand overnight at room temperature, during which the reaction product precipitates in crystalline form. The reaction product is then separated off and dried for 48 hours under nitrogen at 40° C./10 mbar in a vacuum drying cabinet (yield: 91%).

Characterization:

| Mass spectrum: molecular peak at 557 Elemental analysis | |
|---|---|
| Theoretical value (in %) | C: 53.9 H: 2.0 N: 2.5 |
| Found (in %) | C: 53.7 H: 2.1 N: 2.5 | m.p.: 180° C. (decomposition).

EXAMPLE 4

Preparation of benzyl 4-(4-nitro-3-benzyloxyphenoxy)benzoate

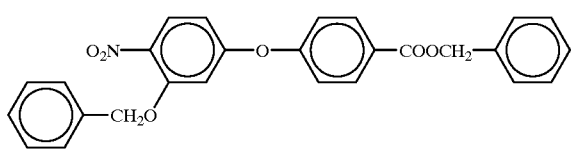

24.7 g of 5-fluoro-2-nitrophenyl benzyl ether (0.1 mol) are dissolved in 250 ml of dimethyl sulfoxide, and a solution of 26.6 g of the potassium salt of benzyl 4-hydroxybenzoate (0.1 mol) in 250 ml of dimethyl sulfoxide is then slowly added drop wise with stirring at room temperature. The mixture is then stirred first at room temperature for 1 hour and then at 50° C. for 24 hours. The reaction solution is then allowed to cool to room temperature and is filtered through a fluted filter, the filtrate is diluted with 700 ml of water, and the crude product is extracted by shaking with 300 ml of ethyl acetate. The organic phase is then washed three times with water, dried over sodium sulfate and evaporated in a rotary evaporator until the reaction product precipitates out. The reaction product is stirred in petrol ether (boiling range 40 to 60° C.) for 2 hours, filtered off via a Büchner funnel and then dried for 48 hours under nitrogen at 40° C./10 mbar in a vacuum drying cabinet (yield: 91%).
Characterization:

| Mass spectrum: molecular peak at 455 Elemental analysis | |
|---|---|
| Theoretical value (in %) | C: 71.2 H: 4.6 N: 3.1 |
| Found (in %) | C: 71.0 H: 4.7 N: 3.0 | m.p.: 96° C.

EXAMPLE 5

Preparation of 4-(4-amino-3-hydroxyphenoxy) benzoic Acid

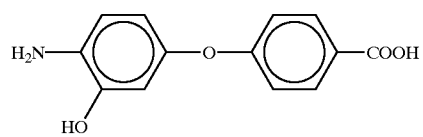

46.6 g of the benzyl 4-(4-nitro-3-benzyloxyphenoxy) benzoate (0.11 mol) prepared as described in Example 4 are dissolved in 500 ml of a mixture of tetrahydrofuran and ethyl acetate (volume ratio 1:1), and 5 g of Pd/C (palladium/carbon) are added to the solution. The mixture is then hydrogenated using hydrogen at a pressure of 1 bar at room temperature in an autoclave with vigorous stirring; the reaction is terminated after 3 days. The pale violet solution is evaporated to half in a rotary evaporator and left to stand overnight at room temperature, during which the reaction product precipitates out in crystalline form. The reaction product is then separated off and dried for 48 hours under nitrogen at 40° C./10 mbar in a vacuum drying cabinet (yield: 93%).

Characterization:

| Mass spectrum: molecular peak at 245 Elemental analysis | |
|---|---|
| Theoretical value (in %) | C: 63.7 H: 4.5 N: 5.7 |
| Found (in %) | C: 63.5 H: 4.5 N: 5.8 | m.p.: 190° C. (decomposition).

EXAMPLE 6

Preparation of 2-(4-benzyloxycarbonylphenoxy)-3,4,5,6-tetrafluoropyridine

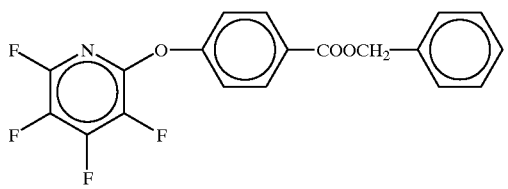

33.8 g of pentafluoropyridine (0.2 mol) are dissolved in 500 ml of dimethylformamide, the solution is cooled to 0° C. by means of a cryostat, and a solution of 53.3 g of potassium 4-benzyloxycarbonylphenoxide (0.2 mol) in 400 ml of dimethylformamide is then added drop wise over the course of 2 hours. After 24 hours at 0° C., the potassium salt has reacted.

The dimethylformamide is then removed in a rotary evaporator, the residue is taken up in a little tetrahydrofuran, and the solution is filtered through a silica-gel column. The clear solution obtained is evaporated in a rotary evaporator until the reaction product precipitates out. The reaction product is then stirred in n-hexane, filtered off via a fluted filter and then dried for 48 hours under nitrogen at 40° C./10 mbar in a vacuum drying cabinet (yield: 91%).

Characterization:

| Mass spectrum: molecular peak at 377 Elemental analysis | |
|---|---|
| Theoretical value (in %) | C: 60.5 H: 2.9 N: 3.7 |
| Found (in %) | C: 60.6 H: 2.9 N: 3.6 |

EXAMPLE 7

Preparation of 4-(4-nitro-3-benzyloxyphenoxy)-2-(4-benzyloxycarbonylphenoxy)-3,5,6-trifluoropyridine

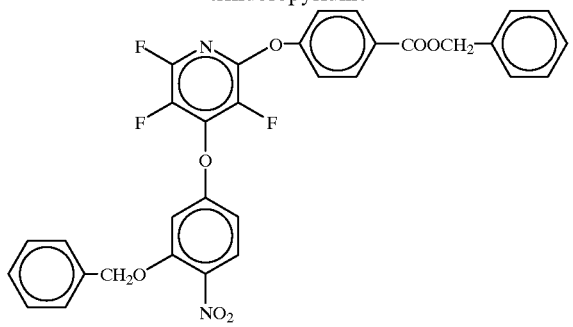

40 g of the 2-(4-benzyloxycarbonylphenoxy)-3,4,5,6-tetrafluoropyridine (0.106 mol) prepared as described in Example 6 and 30 g of potassium 4-nitro-3-benzyloxyphenoxide (0.106 mol) are dissolved in 500 ml of dimethyl sulfoxide. 30 g of potassium carbonate (0.22 mol) are added in portions to the solution. The mixture is then stirred at room temperature for 24 hours, then heated at 60° C. for 24 hours, and 15 g of potassium hydrogencarbonate (0.15 mol) are then added. The reaction solution is then cooled to room temperature and filtered through a fluted filter. The crude product is extracted by shaking with 300 ml of ethyl acetate and 700 ml of water, and the organic phase is washed three times with water and evaporated in a rotary evaporator until the reaction product precipitates out. The reaction product is then recrystallized from a mixture of ethyl acetate and n-hexane (volume ratio 1:1) and then dried for 48 hours under nitrogen at 40° C./10 mbar in a vacuum drying cabinet (yield: 92%).

Characterization:

| Mass spectrum: molecular peak at 602 | |
|---|---|
| Elemental analysis | |
| Theoretical value (in %) | C: 63.8 H: 3.5 N: 4.6 |
| Found (in %) | C: 63.7 H: 3.5 N: 4.6 |

EXAMPLE 8

Preparation of 4-(4-amino-3-hydroxyphenoxy)-2-(4-carboxyphenoxy)-3,5,6-trifluoropyridine

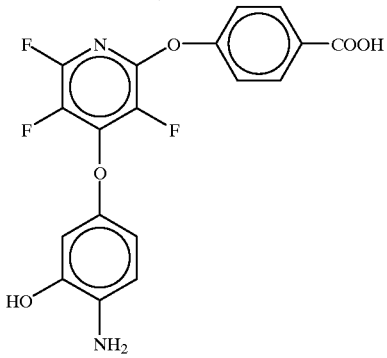

40 g of the 4-(4-nitro-3-benzyloxyphenoxy)-2-(4-benzyloxycarbonylphenoxy)-3,5,6-trifluoropyridine (0.066 mol) prepared as described in Example 7 are dissolved in 600 ml of a mixture of tetrahydrofuran and ethyl acetate (volume ratio 15 1:1), and 4 g of Pd/C (palladium/carbon) are added to the solution. The mixture is then hydrogenated using hydrogen at a pressure of 1 bar at room temperature in an autoclave with vigorous stirring; the reaction is terminated after 3 days. The orange solution is evaporated to half in a rotary evaporator and left to stand overnight at room temperature, during which the reaction product precipitates out in crystalline form. The reaction product is then dried for 48 hours under nitrogen at 40° C./10 mbar in a vacuum drying cabinet (yield: 91%).

Characterization:

| Mass spectrum: molecular peak at 392 | |
|---|---|
| Elemental analysis | |
| Theoretical value (in %) | C: 55.1 H: 2.8 N: 7.1 |
| Found (in %) | C: 55.1 H: 2.8 N: 7.2 |

EXAMPLE 9

Preparation of 2-(4-benzyloxycarbonylphenoxy)-1-trifluoromethyl-3,4,5,6-tetrafluorobenzene

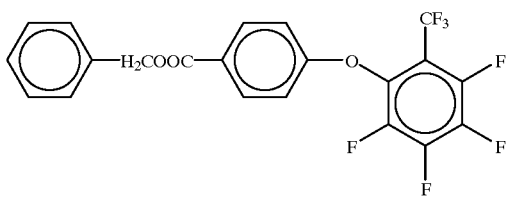

35.4 g of octafluorotoluene (0.15 mol) are dissolved in 400 ml of dimethylformamide, the solution is cooled to 0° C. using a cryostat, and a solution of 40 g of potassium 4-benzyloxycarbonylphenoxide (0.15 mol) in 300 ml of dimethylformamide is then added drop wise over the course of 2 hours. After 24 hours at 0° C., the potassium salt has reacted. The dimethylformamide is then removed in a rotary evaporator, the residue is taken up in a little tetrahydrofuran, and the solution is filtered through a silica-gel column. The clear solution obtained is evaporated in a rotary evaporator until the reaction product precipitates out. The reaction product is then stirred in n-hexane, filtered off through a fluted filter and then dried for 48 hours under nitrogen at 40° C./10 mbar in a vacuum drying cabinet (yield: 95%).

Characterization:

| Mass spectrum: molecular peak at 444 | |
|---|---|
| Elemental analysis | |
| Theoretical value (in %) | C: 56.8 H: 2.5 |
| Found (in %) | C: 56.8 H: 2.5 |

EXAMPLE 10

Preparation of 4-(4-nitro-3-benzyloxyphenoxy)-2-(4-benzyloxycarbonylphenoxy)-1-trifluoromethyl-3,5,6-trifluorobenzene

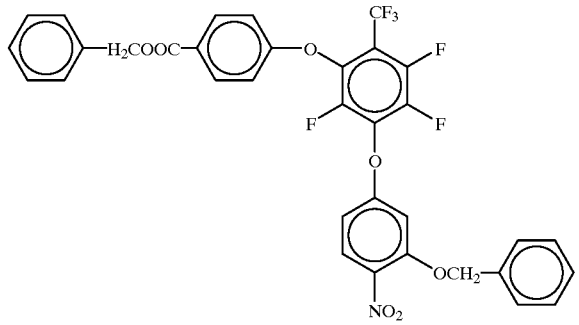

40 g of the 2-(4-benzyloxycarbonylphenoxy)-1-trifluoromethyl-3,4,5,6-tetrafluorobenzene (0.09 mol) prepared as described in Example 9 and 25.5 g of potassium 4-nitro-3-benzyloxyphenoxide (0.09 mol) are dissolved in 400 ml of dimethyl sulfoxide. 30 g of potassium carbonate (0.22 mol) are added in portions to the solution. The mixture is then stirred at room temperature for 24 hours and then heated at 60° C. for 24 hours, and 15 g of potassium hydrogencarbonate (0.15 mol) are then added. The reaction solution is then allowed to cool to room temperature and is filtered through a fluted filter. The crude product is extracted by shaking with 300 ml of ethyl acetate and 700 ml of water, and the organic phase is washed three times with water and evaporated in a rotary evaporator until the reaction product precipitates out. The reaction product is then recrystallized from a mixture of ethyl acetate and n-hexane (volume ratio 1:1) and then dried for 48 hours, under nitrogen at 40° C./10 mbar in a vacuum drying cabinet (yield: 94%).
Characterization:

| Mass spectrum: molecular peak at 669 Elemental analysis | |
|---|---|
| Theoretical value (in %) | C: 61.0 H: 3.2 N: 2.1 |
| Found (in %) | C: 61.1 H: 3.2 N: 2.1 |

EXAMPLE 11

Preparation of 4-(4-amino-3-hydroxyphenoxy)-2-(4-carboxyphenoxy)-1-trifluoromethyl-3,5,6-trifluorobenzene

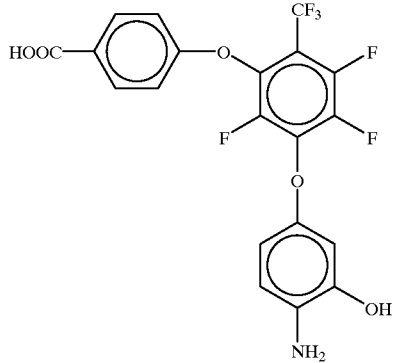

40.4 g of the 4-(4-nitro-3-benzyloxyphenoxy)-2-(4-benzyloxycarbonylphenoxy)-1-trifluoromethyl-3,5,6-trifluorobenzene (0.06 mol) prepared as described in Example 10 are dissolved in 500 ml of a mixture of tetrahydrofuran and ethyl acetate (volume ratio 1:1), and 4 g of Pd/C (palladium/carbon) are added to the solution. The mixture is then hydrogenated using hydrogen at a pressure of 1 bar at room temperature in an autoclave with vigorous stirring; the reaction is terminated after 3 days. The orange solution is evaporated to half in a rotary evaporator and left to stand overnight at room temperature, during which the reaction product precipitates out in crystalline form. The reaction product is then dried for 48 hours under nitrogen at 40° C./10 mbar in a vacuum drying cabinet (yield: 95%).

Characterization:

| Mass spectrum: molecular peak at 459 Elemental analysis | |
|---|---|
| Theoretical value (in %) | C: 52.3 H: 2.4 N: 3.0 |
| Found (in %) | C: 52.3 H: 2.4 N: 3.0 |

We claim:
1. An o-aminophenolcarboxylic acid or o-aminothiophenolcarboxylic acid of the structure

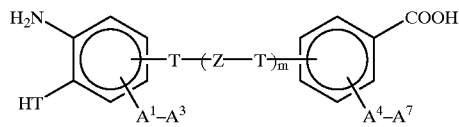

in which:

each of $A^1$ to $A^7$ is a ring substituent independently selected from H, $CH_3$, $OCH_3$, $CH_2CH_3$ or $OCH_2CH_3$;

T is O or S, and m is 1;

Z is one of the following carbocyclic aromatic radicals:

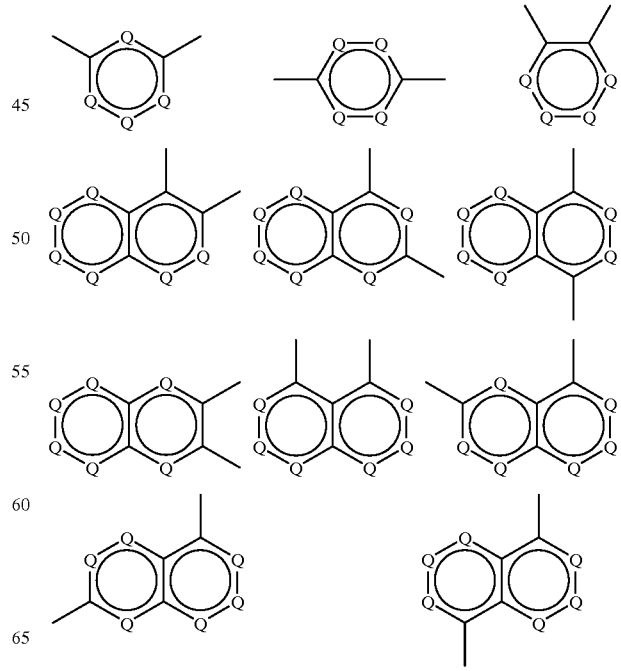

-continued

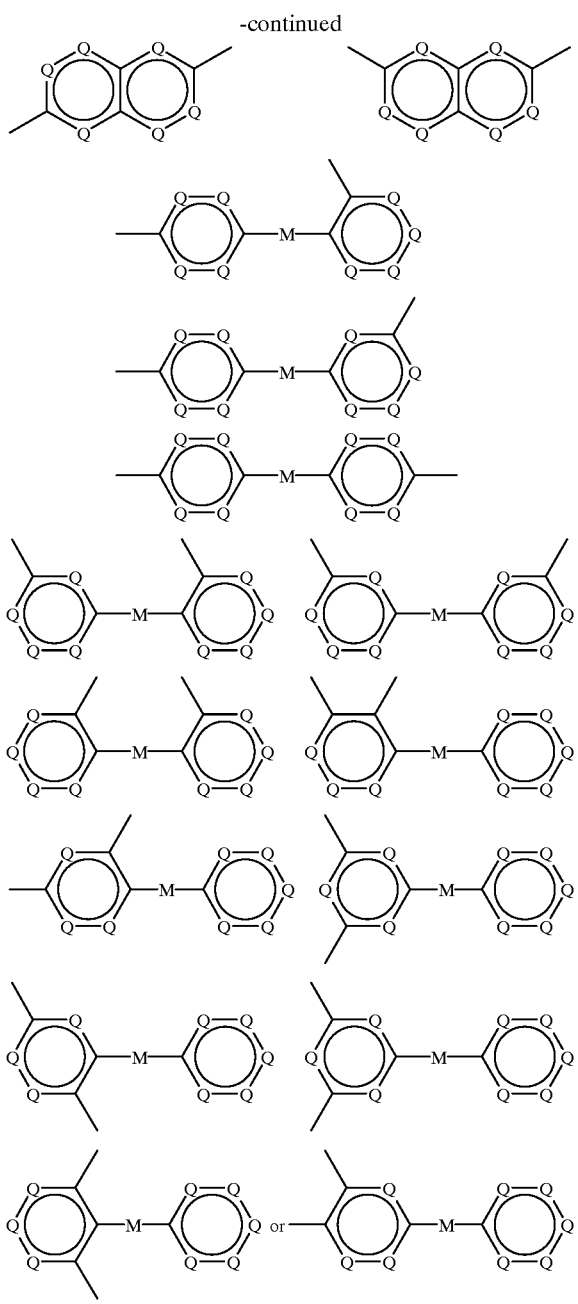

wherein Q=C—A, and A=H, F, $(CH_2)_pCH_3$, $(CF_2)_pCF_3$, $O(CH_2)_pCH_3$, $O(CF_2)_pCF_3$, $CO(CH_2)_pCH_3$, $CO(CF_2)_pCF_3$ where p=0 to 8 (linear or branched chain), $OC(CH_3)_3$, $OC(CF_3)_3$, $C_6H_5$, $C_6F_5$, $OC_6H_5$, $OC_6F_5$, cyclopentyl, perfluorocyclopentyl, cyclohexyl or perfluorocyclohexyl, M=a single bond, $(CH_2)_n$, $(CF_2)_n$, $CH(CH_3)$, $CH(CF_3)$, $CF(CH_3)$, $CF(CF_3)$, $C(CH_3)_2$, $C(CF_3)_2$, $CH(C_6H_5)$, $CH(C_6F_5)$, $CF(C_6H_5)$, $CF(C_6F_5)$, $C(CH_3)(C_6H_5)$, $C(CH_3)(C_6F_5)$, $C(CF_3)(C_6H5)$, $C(CF_3)(C_6F_5)$, $C(CH_5)_2$, $C(C_6F_5)$, CO, $SO_2$,

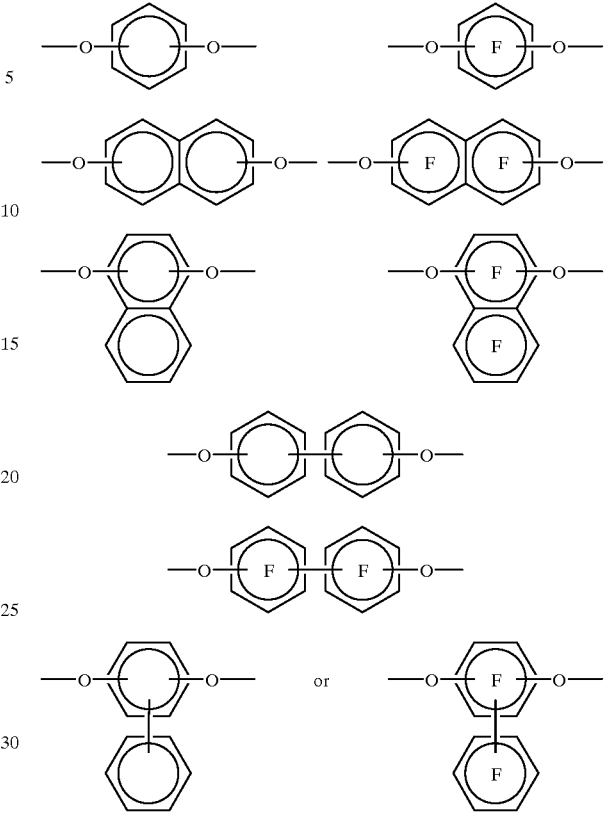

2. An o-aminophenolcarboxylic acid according to claim 1 of the structure

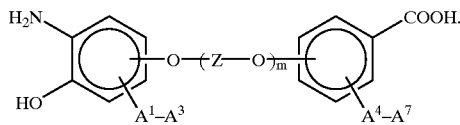

3. An o-aminophenolcarboxylic acid according to claim 2 in which each of $A^1$–$A^3$ and $A^4$–$A^7$ is a hydrogen atom.

4. An o-aminophenolcarboxylic acid according to claim 2 in which m=1 and each carbon atom in Z carries at least one fluorine substituent.

5. An o-aminophenolcarboxylic acid according to claim 4 of the structure

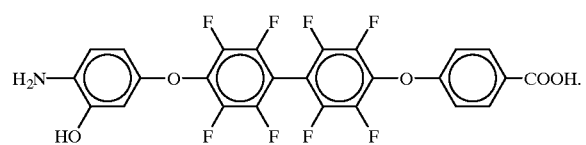

6. An o-aminophenolcarboxylic acid according to claim 4 of the structure

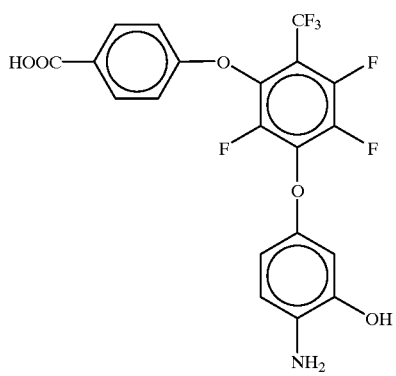

7. A process for the preparation of an o-aminophenolcarboxylic acid or o-aminothiophenolcarboxylic acid as claimed in claim 1, which comprises (a) reacting a halogen compound of the structure

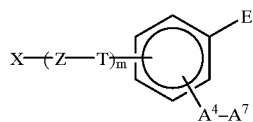

with a nitrophenol or nitrothiophenol of the structure

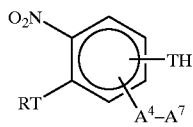

in the presence of at least the stoichiometric amount of a base, or with an alkali metal salt of the nitrophenol or nitrothiophenol, in a solvent at a temperature between −10 and 80° C., where X is a halogen atom, E is CN or $COOR^1$, where $R^1$=alkyl (having 1 to 5 carbon atoms), phenyl or benzyl, $A^1$ to $A^7$, T and Z are as defined above, and R is one of the following radicals: alkyl, alkoxyalkyl, alkenyl, alkoxyalkenyl, alkynyl or alkoxyalkynyl, each having a maximum of 6 carbon atoms, penyl, phenacyl or benzyl, and benzylalkyl, benzylalkenyl, benzyloxyalkyl, benzyloxyalkenyl, benzylalkoxyalkyl or benzylalkoxyalkenyl, each having a maximum of 4 aliphatic rbon atoms; and b) reducing and hydrolyzing the resultant nitro compound to the amino compound and removing the group R.

8. A process for the preparation of an o-aminophenolcarboxylic acid or o-aminothiophenolcarboxylic acid as claimed in claim 1, which comprises (a) reacting a nitro compound of the structure

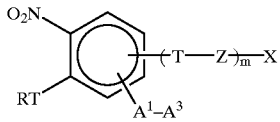

with a phenol or thiophenol of the structure

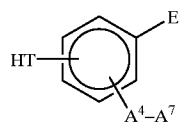

in the presence of at least the stoichiometric amount of a base, or with an alkali metal salt of the phenol or thiophenol, in a solvent at a temperature between −10 and 80° C., where X is a halogen atom, E is CN or $COOR^1$, where $R^1$=alkyl (having 1 to 5 carbon atoms), phenyl or benzyl, $A^1$ to $A^7$, T and Z are as defined above, and R is one of the radicals: alkyl, alkoxyalkyl, alkenyl, alkoxyalkenyl, alkynyl or alkoxyalkynyl, each having a maximum of 6 carbon atoms, phenyl, phenacyl or benzyl, and benzylalkyl, benzylalkenyl, benzyloxyalkyl, benzyloxyalkenyl, benzylalkoxyalkyl or benzylalkoxyalkenyl, each having a maximum of 4 aliphatic carbon atoms; and (b) reducing and hydrolyzing the resultant nitro compound to the amino compound and removing the group R.

9. A process as claimed in claim 7 or 8, wherein the base used is a carbonate or hydrogencarbonate of an alkali metal or alkaline earth metal.

10. A process as claimed in claim 7 or 8, wherein an organic base containing a tertiary N atom is used.

11. A process as claimed in any one of claims 7 to 10, wherein the reduction and the removal of the group R and—if $E=COOR^1$—the hydrolysis are carried out by means of hydrogen and catalyzed by Pd/C.

* * * * *